United States Patent [19]

Gray et al.

[11] 4,223,222
[45] Sep. 16, 1980

[54] SUSPENDED ARM FOR A SCINTILLATION CAMERA

[75] Inventors: David A. Gray, Louisville, Ky.; Marvin L. Sivertsen, Milwaukee, Wis.; Jerome H. Adam, Waukesha, Wis.; John F. Prendergast, Sr., Franklin, Wis.

[73] Assignee: General Electric Company, Milwaukee, Wis.

[21] Appl. No.: 946,586

[22] Filed: Sep. 28, 1978

[51] Int. Cl.³ .......................... G01T 1/20; G12B 9/00
[52] U.S. Cl. ............................ 250/363 S; 250/521
[58] Field of Search .................. 250/360, 363 S, 521, 250/478, 479

[56] References Cited

U.S. PATENT DOCUMENTS

| 3,852,601 | 12/1974 | Casale | 250/363 S |
| 3,983,399 | 9/1976 | Cox, Jr. et al. | 250/363 S |
| 4,012,636 | 3/1977 | Engdahl et al. | 250/363 S |

*Primary Examiner*—Alfred E. Smith
*Assistant Examiner*—Janice A. Howell
*Attorney, Agent, or Firm*—Dana F. Bigelow; Douglas E. Stoner

[57] ABSTRACT

A scintillation camera device has a suspension system for positioning a detector head attached to a suspended arm for imaging a portion of a patient. The suspended arm includes a linking member which is pivotally attached to the suspension system and which extends horizontal from the suspension system. A rigid member is pivotally attached to the linking member and provides horizontal articulation for the suspended arm. The rigid member has a yoke at the end thereof with the yoke having a base with ends adapted to pivotally retain the detector head. The rigid member has a generally arcuate shape which provides clearance for the patient whereby the rigid member can be extended over the patient and lowered for imaging a portion of the far side of the patient. The pivotal attachments of the linking member and the rigid member have releasable brakes to permit ready positioning of the detector head and subsequent locking of the head in that desired position.

10 Claims, 5 Drawing Figures

SUSPENDED ARM FOR A SCINTILLATION CAMERA

BACKGROUND OF THE INVENTION

The present invention relates generally to scintillation cameras, commonly called gamma cameras, and is particularly concerned with the configuration of a suspended arm for supporting a detector head of the camera.

In a diagnostic nuclear medicine, scintillation camera systems are used to detect gamma ray photons emitted from a body in which a radioisotope has been infused. Scintillations occur where photons are absorbed by crystalline material. A typical system is based on the camera of Anger, as disclosed in U.S. Pat. No. 3,011,057. As in the Anger camera, the camera detector head disclosed herein comprises an array of photosensitive devices, such as photomultiplier tubes, having their input ends adjacent to a light plate or disk. Beneath the disk is a scintillation crystal which converts incoming gamma photons into light photons or scintillations. A collimator is interposed between the scintillator and the emitting body so that the emitted photons will impinge substantially perpendicularly to the planer scintillation crystal. The photomultiplier tubes produce a pulse for each scintillation event. Well known electronic circuits are used to produce signals representing the x and y coordinates of the scintillations. A signal is produced which controls a cathode ray oscilloscope display to produce a point of light on its screen at the x and y coordinates corresponding with those of the scintillation event intercepted by the camera. A photographic film may be used as an image integrator of the large number of light spots appearing on the screen on the cathode ray tube. A substantial number of events is required to make up the final picture of radioisotope distribution in the body tissue.

A scintillation camera is commonly mounted as a portable unit which can readily be moved to a patient's bed or other location where a study is to be conducted. The detector head is supported in cantilevered fashion over the patient to be studied. The detector head is movable manually to a desired position.

A particular problem with scintillation cameras of the prior art is illustrated in FIG. 1. The cantilevered support arm extends horizontally from a suspension system to the detector head. It is often desired to image a portion of the far side of the patient. It is readily shown that if the detector head is extended over the patient and lowered for imaging a portion of the far side of the patient, the suspended arm would interfere with the body of the patient (as shown by the hashed lines). It was, therefore, necessary to interrupt the analysis to reposition the camera or the patient in order to image the desired area. This problem was particularly apparent during cardiac analysis where immediately successive images of the right anterior oblique view, vertical view and the left anterior oblique view of the heart are required for proper analysis of cardiac performance.

Another problem with the suspended arm of the prior art was the limited extension and restricted freedom of position of the arm and the detector head. A pair of rigid, horizontal arms were typically provided to position the detector head. The arms had internally telescoping members which provided limited extension and had a pivot for radial positioning. It was frequently necessary to reposition either the patient or the base of the camera for imaging the desired locations of the patient during analysis.

Accordingly, one object of the present invention is to provide a suspended arm for a scintillation camera which can be readily manipulated to position the detector head in desired locations for imaging a patient.

Another object of the present invention is to provide a suspended arm for a scintillation camera which can be manually positioned and readily locked to retain that desired position during analysis of a patient.

SUMMARY OF THE INVENTION

The invention is directed to a suspended arm for use with a scintillation camera device having a suspension system for positioning a detector head attached to the suspended arm for imaging a portion of a patient. The suspended arm includes a linking member which is pivotally attached to the suspension system and which extends horizontal from the suspension system. A rigid member is pivotally attached to the linking member and provides horizontal articulation for the suspended arm. The rigid member has a yoke at the end thereof with the yoke having a base with ends adapted to pivotally retain the detector head. The rigid member has a generally arcuate shape which provides clearance for the patient whereby the rigid member can be extended over the patient for imaging a portion of the far side of the patient. The pivotal attachments of the linking member and the rigid member have releasable brakes to permit ready positioning of the detector head and subsequent locking of the head in that desired position.

BRIEF DESCRIPTION OF THE DRAWINGS

While the novel features of the invention are set forth with particularity in the appended claims, the invention will be better understood, along with other features thereof, from the following detailed description, taken in conjunction with the drawings in which:

DESCRIPTION OF THE PREFERRED EMBODIMENT

Figure 2:
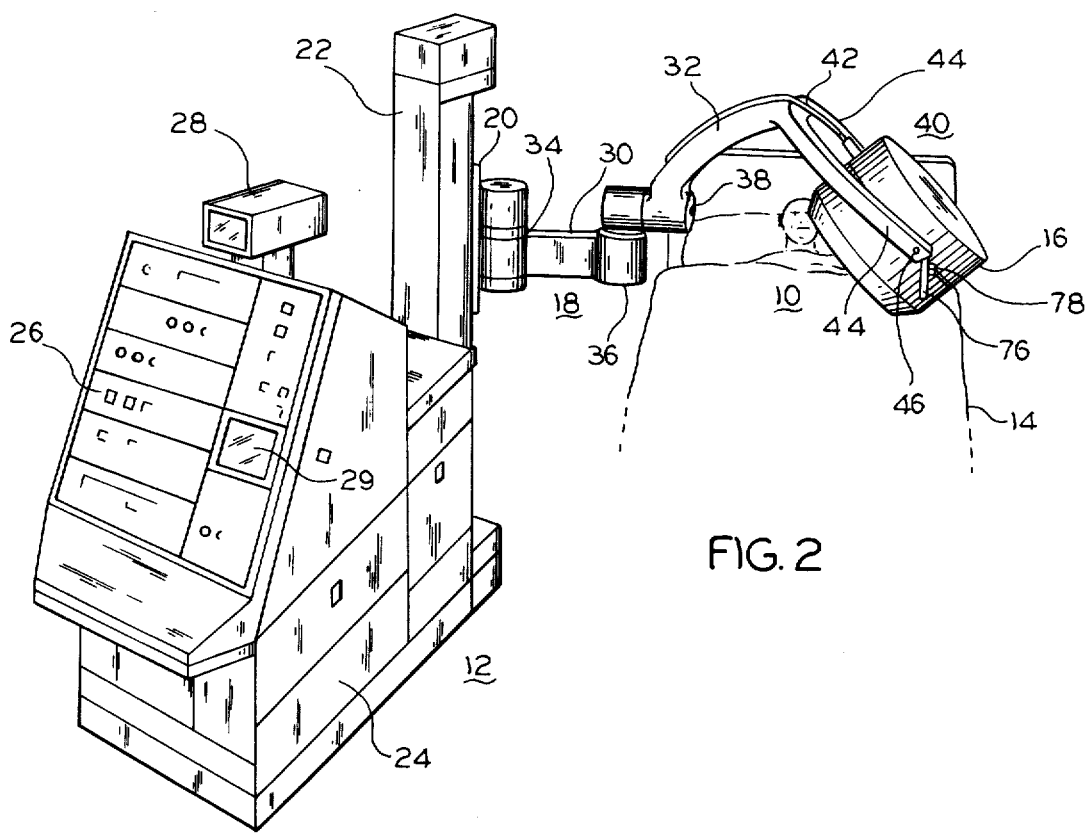
FIG. 2 is a perspective view of a patient undergoing analysis by a scintillation camera incorporating the present invention.
Figure 1:
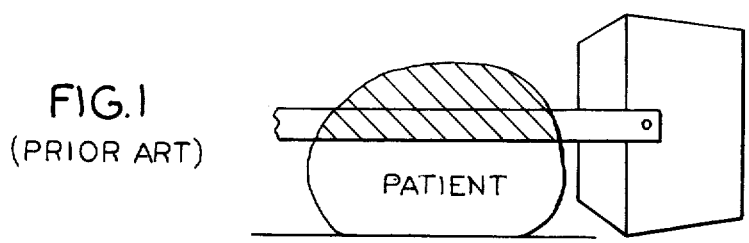
FIG. 1 is a front elevation view showing a support arm of the prior art in interference with a patient while attempting to view the far side of the patient.
Figure 3:
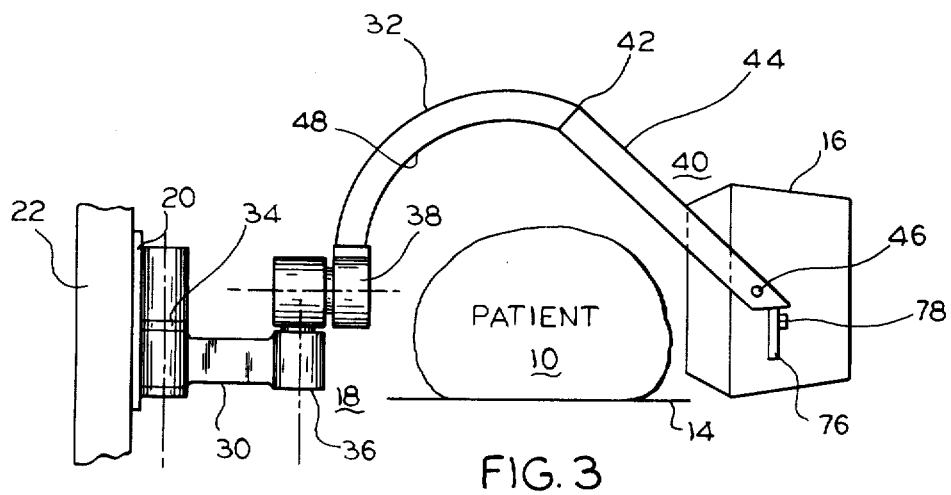
FIG. 3 is a view similar to FIG. 1 showing the clearance of the suspended arm of the present invention, which readily allows a view of the far side of the patient.

Referring first to FIGS. 2 and 3, there is shown a typical example of use of the invention. A patient 10 is shown undergoing analysis by a portable scintillation camera device 12 while being supported by a table 14. During this particular analysis, the patient 10 receives an internal dose of radiopharmaceutical compounds which emit gamma ray energy. The gamma ray energy is detected by a detector head 16 for imaging internal portions of the patient. The detector 16 contains scintillation crystals, photomultiplier tubes, and lead shielding and weighs approximately 230 pounds. The detector head 16 is supported by a suspended arm 18 cantilevered from a suspension system indicated by numeral 20. The suspension system 20 is contained within a vertical column structure 22 and controls the vertical position of the detector head 16 at desired positions along the vertical column structure. A suitable suspension system is shown in copending U.S. patent application Ser. No. 921,197, entitled "Safety Catch Apparatus for a Suspension System", and is assigned to the assignee of the present invention. The details of the suspension system generally include a ⅛ inch aircraft cable which extends from suspended arm 18 upward to a follower pulley, having a brake control to lock the vertical position, and downward to a counterpoised device. A suitable counterpoised device is shown in U.S. Pat. No. 4,003,552 to Sobolewski and is also assigned to the assignee of the present invention.

A main chassis of the scintillation camera device is indicated by numeral 24 and houses the mechanism and electronics for powering and controlling the device. A control console 26 contains camera electronics, drive controls, imaging oscilloscopes and controls for accessory equipment for data analysis. The diagnostic image from detector head 16 is displayed at persistence oscilloscope 28 and at a photo display oscilloscope 29. A variety of well known scintillation camera devices having a variety of suspension systems could utilize the suspended arm of the present invention.

In accordance with the present invention, a linking member 30 is interconnected between the suspension system 20 and an arcuate rigid member 32. One end of linking member 30 is attached to the suspension system 20 by a vertical pivotal union 34 which allows the linking member to be rotatable about the union in the horizontal plane. The other end of linking member 30 is attached to rigid member 32 by another vertical pivotal union 36. The attachments at pivotal unions 34 and 36 allow the linking member and the rigid member to be articulated in the horizontal plane which extends the reach and facilitates positioning of the detector head.

Figure 4:
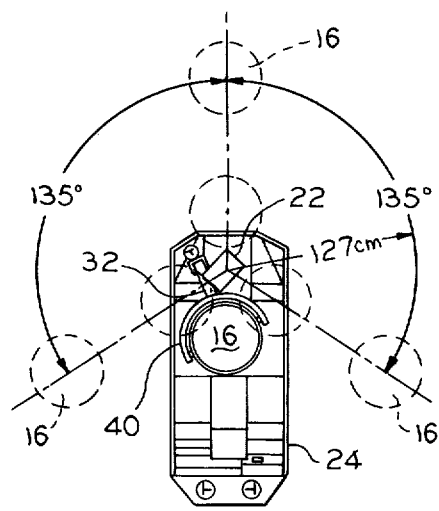
FIG. 4 is a reduced plan view of the device shown in FIG. 1 which shows the range of locations for positioning the suspended arm.

Referring particularly to FIG. 4, it is shown that the articulation of the suspended arm 18 permits the detector head 16 to be positioned immediately adjacent the column structure 22 or fully extended 127 cm from the column structure. In the fully extended position, the detector head can be rotated 135° in either direction from a central position about the column structure 22. This feature permits the detector head 16 to be operably placed at any intermediate position within the 127 cm radius and inscribed by the 270° arc. The articulation also permits the detector head to be positioned over the main chassis 24 (as shown) for transporting or storing the device. This flexibility and reach of the suspended arm 18 provides a distinct advantage for the camera device 12. Access to the bed of a patient is often limited. The portable camera device can be positioned at any location convenient to the patient's bed. The device can be positioned close to the patient with the arm articulated for imaging the near portions of the patient, the arm can subsequently be extended for imaging other portions of the patient without repositioning the patient or the base of the device.

Referring again to FIGS. 2 and 3, rigid member 32 is shown attached to the vertical pivotal union 36 by an interconnecting horizontal pivotal union 38. Pivotal union 38 allows the rigid member 32 to be rotated ±180° from a vertical position about the pivotal union. The other end of rigid member 32 forms a yoke 40 having a base 42 and extended ends 44. Extended ends 44 are adapted to pivotally retain the detector head 16 at points 46 in trunnion fashion, allowing 360° rotation by the detector head within the yoke 40.

Rigid member 32 has a shape which provides clearance for the patient 10 so that the suspended arm can be extended over the patient. The suspended arm and detector head can then be lowered for imaging a portion of the far side of the patient without interfering with or injuring the patient. Rigid member 32 has a generally arcuate shaped portion 48 which extends from pivitol union 38 generally upwardly to the base 42 of yoke 40. The yoke 40 extends from base 42 generally downwardly so that pivot point 46 is generally positioned in horizontal alignment with pivital union 38. Pivot point 46 is precisely positioned so that the center of balance of rigid member 32 and detector head 16 is aligned with pivital union 38 so that the rigid member will be balanced and stable in any desired position. As shown, arcuate shaped portion 48 is formed having an approximate 38 cm radius generally concentric with the patient and extends upwardly 38 cm above union 38. Yoke 40 is actually flat for convenience of manufacture but could alternately have a arcuate shape similar to portion 48. Rigid member 32 provides clearance of approximately 63 cm between union 38 and pivot point 46 with an approximate upper radial clearance of 35 cm, which is adequate clearance for even an extremely oversized patient.

Rigid member 32 is uniquely fabricated with consideration given to both strength and appearance. The arcuate shaped portion 48 is fabricated into a 1½"×3"×3" tube having a wall thickness of one-eighth inch. The tube is fabricated from four pieces of Cor-Ten steel. The upper and lower arcuate pieces are rolled to the proper curvature. The curved pieces and the conforming side pieces are all welded together to form the tube. The Yoke 40 is similarly fabricated into a 1½"×2½" tube having a wall thickness of one-eighth inch. One piece of Cor-Ten steel is formed into a channel and rolled into a 180° arc having a radius conforming to the diameter of the detector head, which in this embodiment is 29 cm. The outer arcuate wall is rolled into the proper curvature and welded to the channel to form the tubular yoke. Solid blocks of A36 steel are used to tie the arcuate portion 38 to the Yoke 40 and are solidly welded together. Steel blocks are also used to reinforce the pival attachments at 38 and 46. After the parts are assembled, the welds are all radiographed for compliance to the welding code and are magnafluxed to assure quality. In other embodiments, graphite composition material could be used to form rigid member 32. The weight of the suspended arm is extremely significant because of the relationship to the requirements of the suspension system and to the overall weight of the device which must be within capacity limits of hospital elevators. The rigid member, fabricated as described above, weighs approximately 60 pounds and can support four times the weight of the detector head for a comfortable safety factor. Rigid member 32 could alternatively be fabricated by a variety of methods and materials having a variety of shapes, such as an inverted "V", "U" or "C" shape to provide clearance for the patient.

The detector head 16 is adapted to be pivotally supported at point 46 of the member 32. The trunnions of the detector for mounting at point 46 are at the center of balance of the detector head. Points 46 include conventional bearings and an internal resistance which acts as a friction brake for the detector head. The detector head requires a nominal force of approximately three pounds to position it at any of the desired 360° positions and it remains balanced and fixed at that position until repositioned by the operator.

Figure 5:
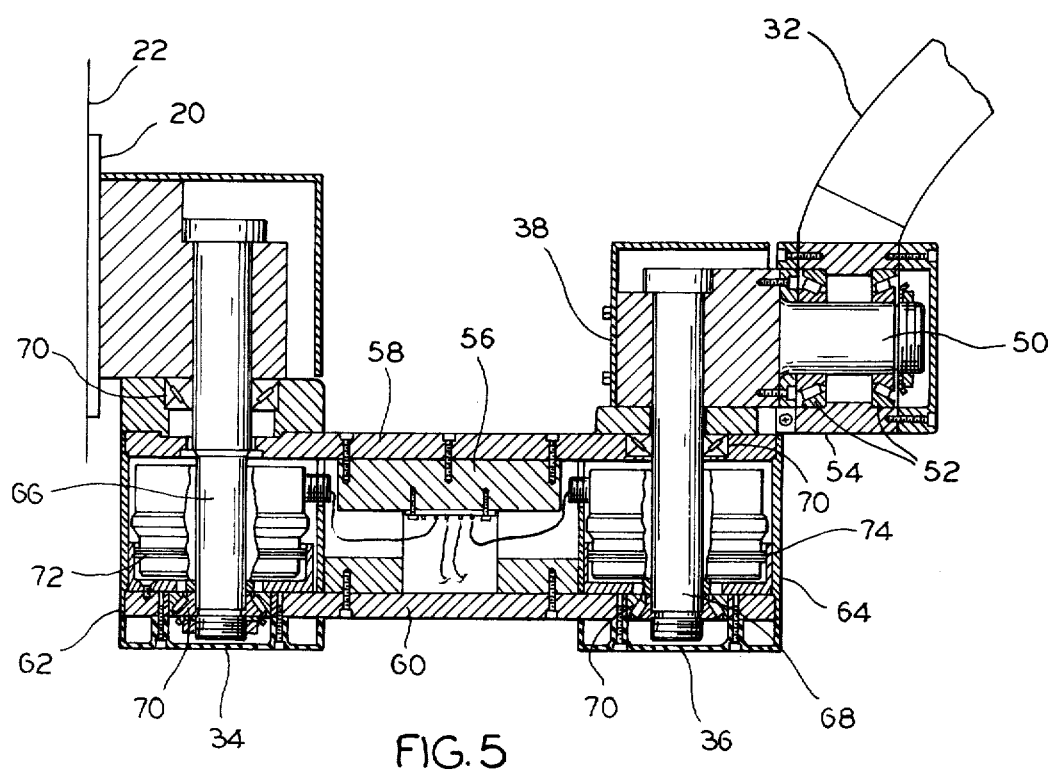
FIG. 5 is a sectional view of the suspended arm shown in FIG. 3.

Referring now to FIG. 5, horizontal pivotal union 38 is shown as a conventional pivotable connection having a central shaft 50 mounted in a pair of "Timken" bearings 52 within the pivotal union housing 54. The clearance and internal resistance are established to form a friction brake which retains the rigid member 32 at any set angulated position. This positioning system is possible because the weight of the detector head 16 is carried at the pivotal point 46 which is in general horizontal alignment with the pivotal union 38. The weight of the detector 16 and the member 32 are concentricly balanced around union 38 so that the detector head is stabilized at any of the ±180° positions of the rigid member. Similarly as for the detector head, a force of approximately three pounds is required to overcome the resistance of the frictional brake of union 38 to reposition rigid member 32. Rigid member 32 will remain balanced and fixed at any set position until it is repositioned by the operator.

Linking member 30 is fabricated from an aluminum block 56 having a top access plate 58 and a lower plate 60. The block 56 is machined to form the housings 62 and 64 for pivotal unions 34 and 36. The aluminum construction provides a strong, rigid linking member which is extremely light weight. Vertical pivotal unions 34 and 36 are also conventional pivotal connections having a central shaft 66 and 68 retained within "Timken" bearings 70 of the union housings 62 and 64. The central shafts 66 and 68 as well as shaft 50 are each fabricated from 4340 annealed steel which are hardened and ground to "Rockwell C"—R50 to R55. Each vertical pivotal union 34 and 36 contain a cup and brake assembly 72 and 74 which is electrically actuated and de-actuated to lock the position of the linking member 30 and the rigid member 32 relative to the suspension system 30. A suitable cup and brake assembly is available from Carlyle-Johnson Machine Co., Manchester, Conn., part No. 46-402498 pol. The brakes 72 and 74 of pivotal unions 34 and 36 are adjusted so that they may be manually overcome by a horizontal force of approximately eight pounds. This is to insure that in the event of an emergency or electrical failure the operator can readily reposition the detector head if necessary without electrical power. All of the pivotal unions of the suspension arm are fabricated and assembled to very close tolerances so that there is no excessive play or unwanted movement at the detector head.

Referring again to FIG. 3, in order to facilitate the positioning of the detector head a handle 76 is provided at the end of each extended end 44 of yoke 40. The handles can be easily grasped by the operator to manually manipulate the detector head into the desired position. Each handle includes a switch 78 which controls the electrically actuated and de-actuated brakes 72 and 74 within pivotal union 34 and 36 and also controls the brake located in the follower pulley of the suspension system 20. It is readily seen that an operator could easily grasp either of handles 76 and press switch 78 whereby the detector head is free to be positioned at any desired location relative to the patient. The linking member and rigid member can be articulated to the proper lateral position then the suspension system can be lowered to the desired elevation relative to the patient. Rigid member 32 could be angulated and detector head 16 could also be pivoted about pivot point 46 to place the detector head in the precise position to image the desired portion of the patient. Switch 78 is then put in the locked position to lock vertical pivotal unions 34, 36 and the suspension system while the friction brakes lock horizontal pivotal union 38 and points 46 to fix the detector head in the desired position. Upon completion of the desired image the operator can again grasp handle 76 and repeat the repositioning procedure for any other desired position. It is realized that in other embodiments, all of the pivotal unions could be retained by frictional brakes or all could be retained by electrically actuated and de-actuated brakes or in some cases could be positioned without a deliberate locking or braking system.

In accordance with the present invention a suspended arm for a scintillation camera has been described which can be positioned at any desired location for imaging the patient. The suspended arm can be manually positioned and readily locked to retain that desired position during analysis of the patient.

While a specific embodiment of the present invention has been illustrated and described herein, it is realized that modifications and changes will occur to those skilled in the art. It is, therefore, to be understood that the appended claims are intended to cover all such modifications and changes as fall within the true spirit and scope of the invention.

What is claimed is:

1. A suspended arm for use with a scintillation camera device having a suspension system for positioning a detector head attached to said suspended arm for imaging a portion of a patient, said suspended arm comprising:

a rigid member having a yoke at one end thereof, said yoke having a base with ends adapted to pivotally retain the detector head at pivot points, and means for attaching the other end of said rigid member to the suspension system, said rigid member having a shape which extends from said attaching means generally upwardly to the base of said yoke and extends from the base of said yoke generally downwardly to the ends thereof to provide clearance for the patient between said attaching means and said pivot points whereby said rigid member can be extended over the patient for imaging a portion of the far side of the patient.

2. The suspended arm as recited in claim 1 wherein said rigid member has a generally arcuate "c" shape between said attaching means and the detector head.

3. The suspended arms as recited in claim 1 wherein the attaching means includes a horizontal pivotal union for angulating the rigid member.

4. The suspended arms as recited in claim 3 wherein the attaching means further includes a vertical pivotal union for horizontally pivoting the detector head.

5. The suspended arm as recited in claim 3 wherein the attaching means further includes a linking member having a vertical pivotable union at each end thereof with said linking member interposed between the suspension system and said rigid member and thereby provides horizontal articulation which extends the reach and facilitates the positioning of the detector head.

6. A suspended arm for use with a scintillation camera device having a suspension system for positioning a detector head attached to said suspended arm for imaging a portion of a patient, said suspended arm comprising:
 a linking member pivotally attached to the suspension system and extending horizontally therefrom,
 a rigid member pivotally attached to said linking member and extending therefrom,
 said rigid member having a yoke at the end thereof with said yoke having a base with end pivot points adapted to pivotally retain the detector head,
 said rigid member having a shape which extends from said attaching means generally upwardly to the base of said yoke and extends from the base of said yoke generally downwardly to the ends thereof to provide clearance for the patient between said attaching means and said pivot points whereby said rigid member can be extended over the patient for imaging a portion of the far side of the patient.

7. The suspended arm as recited in claim 6 wherein said rigid member extends from said pivotally attached end in an arcuate shape which is generally concentric with the contour of the patient, to the base of said yoke.

8. The suspended arm as recited in claim 6 which further comprises means for manually articulating the pivotal attachments of said linking member and said rigid member to position the detector head in a desired position.

9. The suspended arm as recited in claim 7 wherein said articulating means includes a releasable brake for pivotal attachments of said linking member and said rigid member to fix the detector head in the desired position.

10. The suspended arm is recited in claim 6 wherein said pivot points are precisely positioned such that the center of balance of said rigid member is aligned with said linking member such that the rigid member will be balanced and stable in any desired position.

* * * * *